US011361860B2

(12) United States Patent
 Ali

(10) Patent No.: US 11,361,860 B2
(45) Date of Patent: Jun. 14, 2022

(54) SYSTEM AND METHOD FOR AUTHENTICATING MEDICAL DEVICE DISPOSABLE COMPONENTS

(71) Applicant: Fenwal, Inc., Lake Zurich, IL (US)

(72) Inventor: Zahra R. Ali, Chicago, IL (US)

(73) Assignee: Fenwal, Inc., Lake Zurich, IL (US)

( * ) Notice: Subject to any disclaimer, the term of this patent is extended or adjusted under 35 U.S.C. 154(b) by 121 days.

(21) Appl. No.: 16/023,484

(22) Filed: Jun. 29, 2018

(65) Prior Publication Data

US 2019/0006039 A1 Jan. 3, 2019

Related U.S. Application Data

(60) Provisional application No. 62/526,784, filed on Jun. 29, 2017.

(51) Int. Cl.
*G16H 20/40* (2018.01)
*G16H 40/40* (2018.01)
(Continued)

(52) U.S. Cl.
CPC .......... *G16H 20/40* (2018.01); *A61M 1/0209* (2013.01); *A61M 1/3683* (2014.02); *G16H 40/40* (2018.01);
(Continued)

(58) Field of Classification Search
CPC ..... G16H 20/40; G16H 40/40; A61M 1/0209; A61M 1/3683; A61M 2205/6063;
(Continued)

(56) References Cited

U.S. PATENT DOCUMENTS 5,868,696 A 2/1999 Giesler et al.
6,027,657 A 2/2000 Min et al.
(Continued)

FOREIGN PATENT DOCUMENTS

EP 2774685 A1 9/2014
EP 3040093 A1 7/2016
(Continued)

OTHER PUBLICATIONS

Dymex. "Encompass Technology Speed Up Your Process and Safeguard Against Incomplete Cures" Jun. 6, 2017. (https://web.archive.org/web/20170606191736/https://dymax.com/adhesives/encompass) (Year: 2017).*
(Continued)

*Primary Examiner* — Christopher L Gilligan
*Assistant Examiner* — Chance L Smith
(74) *Attorney, Agent, or Firm* — Cook Alex Ltd.

(57) ABSTRACT

A computer-implemented method for approving a medical device disposable component used in a medical procedure comprising providing an identifiable feature on a medical device disposable component, wherein the identifiable feature comprises one or more photo-identifiable entities having a first emission pattern when in an unexcited state and a second emission pattern when in an excited state. The method also comprises illuminating the identifiable feature with an excitation light source to elicit the second emission pattern, detecting the second emission pattern and comparing the second emission pattern against a set of established reference emission patterns, and determining whether the medical device disposable component is approved based on comparison of the second emission pattern to the set of established reference emission patterns.

21 Claims, 9 Drawing Sheets

(51) Int. Cl.
  *A61M 1/36* (2006.01)
  *A61M 1/02* (2006.01)
(52) U.S. Cl.
  CPC .............. *A61M 2205/6063* (2013.01); *A61M 2205/6072* (2013.01)
(58) Field of Classification Search
  CPC  A61M 2205/6072; G06F 19/30; G06F 19/32; G06F 19/34; G06Q 50/22; G06Q 50/24
  See application file for complete search history.

(56) References Cited

U.S. PATENT DOCUMENTS

| | | | | |
|---|---|---|---|---|
| 6,190,609 | B1* | 2/2001 | Chapman | A61L 2/0011 422/24 |
| 7,079,230 | B1* | 7/2006 | McInerney | G06K 7/12 356/71 |
| 7,433,030 | B2* | 10/2008 | Waldo | A61L 2/0011 356/218 |
| 10,434,239 | B1* | 10/2019 | Briggs | A61M 1/3683 |
| 2008/0311495 | A1* | 12/2008 | Norsten | C07D 491/10 430/19 |
| 2009/0166427 | A1 | 7/2009 | Chambers | |
| 2015/0310454 | A1* | 10/2015 | Ranieri | G06Q 50/22 348/161 |

FOREIGN PATENT DOCUMENTS

| | | | |
|---|---|---|---|
| WO | 2012125457 | A1 | 9/2012 |
| WO | 2016057956 | A1 | 4/2016 |
| WO | WO-2016057956 | A1 * | 4/2016 ............ G06F 21/10 |
| WO | 2017102723 | A1 | 6/2017 |

OTHER PUBLICATIONS

Miao Wang, et al., Nanomaterial-based barcodes, Nanoscale, May 25, 2015, 7, 11240-11247.
Extended European Search Report for counterpart EP Application No. 18179551 (dated Nov. 26, 2018) (8 pages).

* cited by examiner

US 11,361,860 B2

SYSTEM AND METHOD FOR AUTHENTICATING MEDICAL DEVICE DISPOSABLE COMPONENTS

CROSS-REFERENCE TO RELATED APPLICATIONS

This application claims the benefit of U.S. Provisional Patent App. No. 62/526,784 filed Jun. 29, 2017, which is expressly incorporated herein by reference in its entirety.

FIELD OF THE DISCLOSURE

The present disclosure relates generally to methods, systems, and apparatus to authorize a medical device instrument and, in particular, to methods, systems, and apparatus to authenticate usage of a disposable component in a medical device instrument with UV irradiation.

BACKGROUND

Light irradiation therapy may be used for the treatment of various blood diseases to, e.g., eliminate immunogenicity in cells, inactivate or kill selected cells, inactivate viruses or bacteria, and/or activate desirable immune responses. For example, the photoactivatable drug psoralen may be used to treat pathogenic blood cells, such as lymphocytes, in an extracorporeal photopherisis (ECP) procedure in which the patient receives 8-methoxypsoralen (8-MOP), blood is withdrawn from the patient, the white cells separated (typically by centrifugation), and subjected to UV light to activate the 8-MOP molecules. The photoactivated 8-MOP may alter the DNA of the pathogenic leukocytes, and the fluid with the altered leukocytes may be reinfused back into the patient to induce an immune system response.

Light irradiation therapy may be performed by a medical device instrument, such as an apheresis instrument. An apheresis instrument may be used to separate blood components from whole blood by passing blood of a donor/patient through the instrument to separate one or more blood components from the whole blood. The remainder of the whole blood may be returned to the circulatory system of the donor/patient and/or collected.

The medical device instrument may utilize a centrifuge and/or membrane separator to separate blood components. A disposable component may be connected to the instrument for collection of a desired blood component. The instrument hardware may have pumps, clamps, and valves that move and direct fluid or blood through the disposable component. Part of the disposable component may include a bag into which the desired blood component is collected for light irradiation therapy.

SUMMARY

According to an exemplary embodiment, the present disclosure is directed to a computer-implemented method for approving a medical device disposable component used in a medical procedure comprising providing an identifiable feature on a medical device disposable component, wherein the identifiable feature comprises one or more photo-identifiable entities having a first emission pattern when in an unexcited state and a second emission pattern when in an excited state. The method also comprises illuminating the identifiable feature with an excitation light source to elicit the second emission pattern, detecting the second emission pattern and comparing the second emission pattern against a set of established reference emission patterns, and determining whether the medical device disposable component is approved based on comparison of the second emission pattern to the set of established reference emission patterns.

According to an exemplary embodiment, the present disclosure is directed to a medical device authentication and authorization system during a medical procedure comprising a durable medical device comprising an excitation light source and at least one irradiation receiver. The system also comprises a fluid circuit configured to cooperatively associate with the durable medical device, the fluid circuit comprising a disposable component having an identifiable feature comprising one or more photo-identifiable entities having a first emission pattern when in an unexcited state and a second emission pattern when in an excited state. The system also comprises a programmable controller configured to illuminate the identifiable feature with the excitation light source to elicit the second emission pattern, detect the second emission pattern with the at least one irradiation receiver, compare the second emission pattern against a set of established reference emission patterns, and determine whether the disposable component is approved based on comparison of the second emission pattern to the set of established reference emission patterns.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

DETAILED DESCRIPTION

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

Some embodiments may prevent use of counterfeit, already-used, and/or repurposed disposable components.

Some embodiments may prevent instrument use in an unintended manner, e.g., online use versus offline use.

Some embodiments may enable instrument and/or disposable component authentication with minimal user knowledge.

Some embodiments may increase difficulty in replicating authenticity markers and thereby improve copycat protection for disposable components.

Some embodiments may increase longevity of authenticity markers of disposable components.

Some embodiments may obviate a dedicated light source for scanning and/or authentication purposes.

Figure 1:
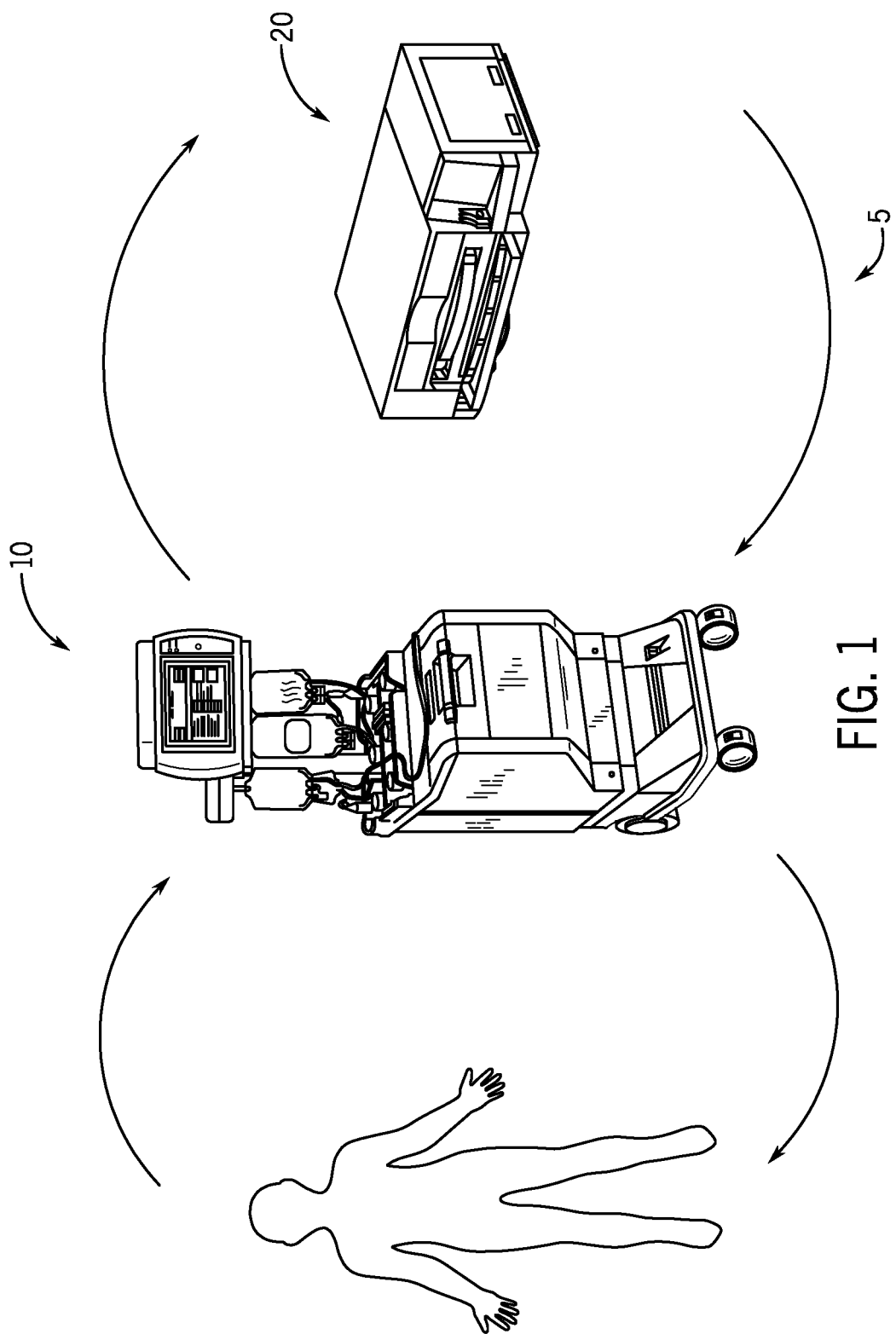
FIG. 1 is a diagram generally showing the mechanical components of a photopheresis treatment device, according to an exemplary embodiment.
Figure 2:
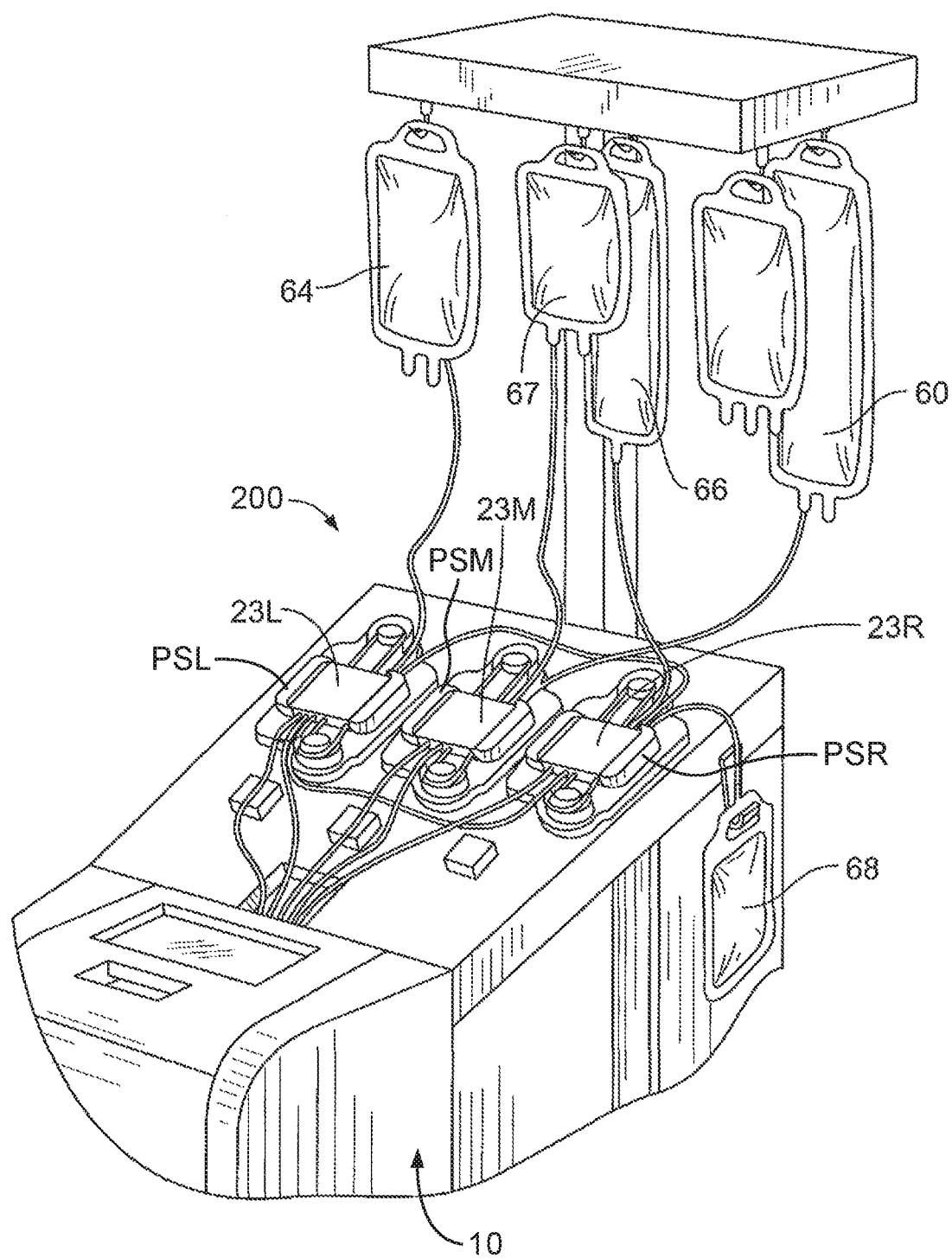
FIG. 2 is a partial perspective view of an apheresis separator useful in the methods and systems described herein, according to an exemplary embodiment.
Figure 4:
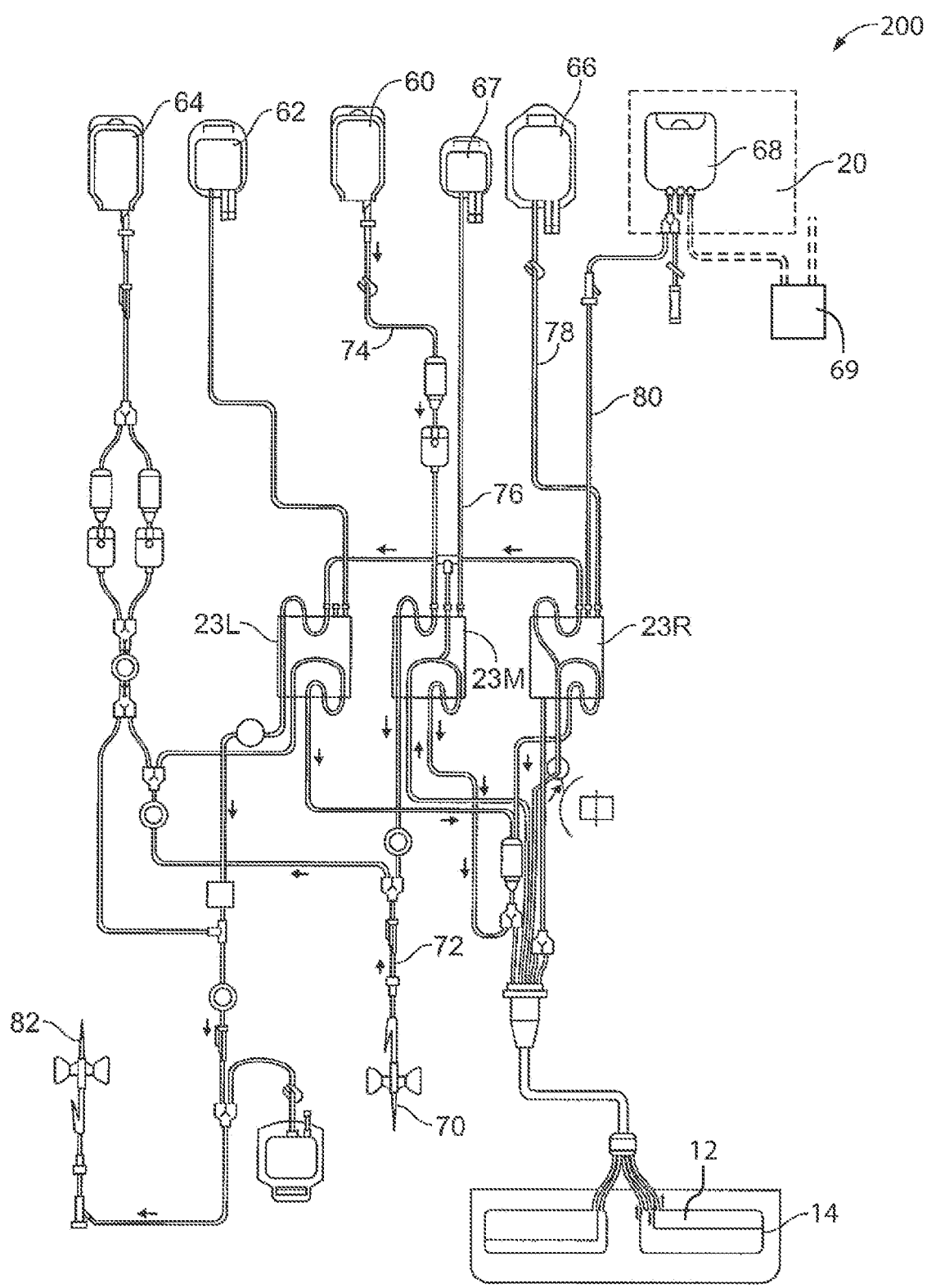
FIG. 4 is a diagram of the fluid circuit useful in the collection, treatment and reinfusion of target cells; according to an exemplary embodiment.

FIG. 1 shows, in general, the mechanical components that make up an ECP system 5 and that may be used in one or more of the methods described herein. The system 5 may include a separation component 10 and a treatment (i.e., irradiation) component 20. Irradiation component 20 may be independent and housed separately from the separation component 10, or components 20 and 10 may be integrated into a single device. In an embodiment in which components 20 and 10 are housed separately, the separation device 10 and irradiation device 20 may be located adjacent to each other, allowing an operator or clinician to have access to both devices during a particular treatment procedure. A patient may be connected to a fluid circuit 200 as shown in FIGS. 1, 2, 4 that provides a sterile closed pathway between separation component 10 and irradiation component 20 and may be cooperatively mounted on the hardware of the separation device 10. The separation device 10 may have one or more features of an apheresis device, such as those described in greater detail in U.S. Pat. Nos. 5,868,696 and 6,027,657, and PCT Patent Application No. PCT/US2012/28492, which are hereby incorporated herein by reference in their entireties, although any suitable separation device may be used. Although the embodiments disclosed herein are described in conjunction with a separation device 10, the present embodiments may be applicable to an irradiation device 20 alone, in which case the target cell population may be provided to the irradiation device 20 subsequent to being collected elsewhere. While improved authorization/authentication systems and methods will be described herein with reference to apheresis and photopheresis, it should be understood that these principles may be employed with other medical procedures involving a specific range of light frequencies without departing from the scope of the present disclosure.

With reference to FIG. 1, whole blood may be withdrawn from the patient and introduced into the separation component 10 where the whole blood is separated to provide a target cell population. In one embodiment, the target cell population may be mononuclear cells (MNCs) or MNCs of a particular type (lymphocytes, monocytes, and/or dendritic cells, etc.). Other components separated from the whole blood, such as red blood cells (RBCS), plasma, and/or platelets may be returned to the patient or collected in pre-attached containers of the blood processing set.

The separated target cell population, e.g., mononuclear cells, may then be treated and irradiated in treatment component 20. As discussed above, treatment of mononuclear cells may involve the photoactivation of a photoactive agent that has been combined with the mononuclear cells. Mononuclear cells may be collected using a device described in greater detail in the aforementioned U.S. Pat. No. 6,027,657. The apparatus used for the harvesting, collection and reinfusion of mononuclear cells may be a "multifunctional" automated apheresis device, as is the case with that described in U.S. Pat. No. 6,027,657. In other words, the separation component 10 may be a multifunctional automated apparatus that can perform various collection protocols and/or serve multiple purposes, as may be needed by a particular hospital or facility, such that it can be used not only in the systems and methods for performing photopheresis treatment of MNC as described herein, but can also be used for other purposes including the collection of blood and blood components including platelets, plasma, red blood cells, granulocytes and/or perform plasma/RBC exchange, among other functions required by a hospital or medical facility.

Figure 3:
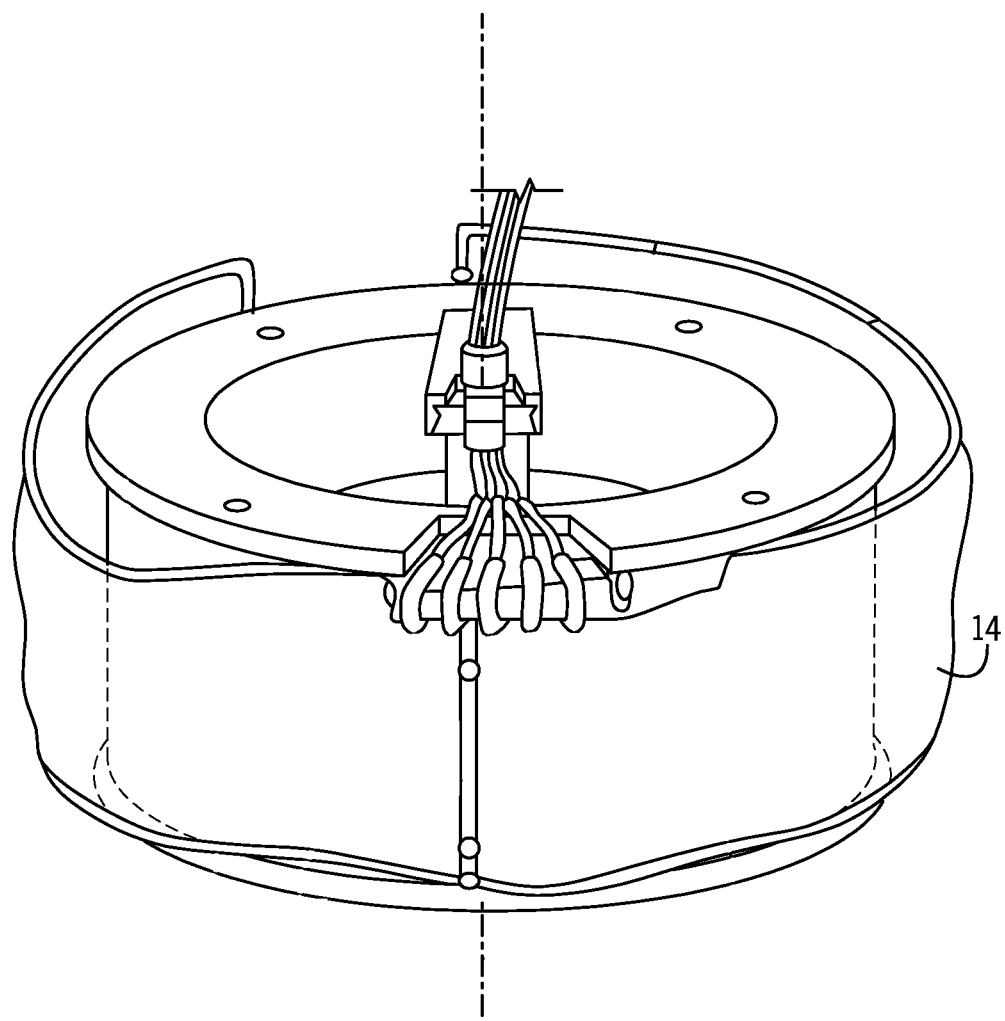
FIG. 3 is a perspective view of a separation chamber of the processing set used with the separator of FIG. 2, according to an exemplary embodiment.

FIGS. 2-4 depict a separator 10 with fluid circuit 200 mounted thereon (FIG. 2), the fluid circuit (FIG. 4) having a blood processing container 14 (FIG. 3) defining a separation chamber 12 suitable for harvesting mononuclear cells (MNC) from whole blood. As shown in FIG. 2, a disposable processing set or fluid circuit 200 (which includes container 14) may be mounted on the front panel of separator 10. The fluid circuit 200 may include a plurality of processing cassettes 23L, 23M and 23R with tubing loops for association with peristaltic pumps on separator 10. Fluid circuit 200 may also include a network of tubing and pre-connected containers for establishing flow communication with the patient and for processing and collecting fluids and blood and blood components, as shown in FIG. 4. As seen in FIGS. 2 and 4, disposable processing set 200 may include a container 60 for supplying anticoagulant, a waste container 62 for collecting waste from one or more steps in the process for treating and washing mononuclear cells, a container 64 for holding saline or other wash or resuspension medium, a container 66 for collecting plasma, a container 68 for collecting the mononuclear cells and, optionally, container 69 for holding the photoactivation agent.

Container 68 may also serve as the illumination container, and the illumination container 68 may be pre-attached to and integral with the disposable set 200. Alternatively, container 68 may be attached to set 200 by known sterile connection techniques, such as sterile docking or the like. In FIG. 2, container 68 is shown as suspended from device 10. However, container 68 may be housed within an adjacent separately housed irradiation device 20 (as shown by broken lines in FIG. 4), thereby eliminating the step of having the operator place container 68 into irradiation device 20. The tubing leading to and/or from container 68 in fluid circuit 200 may be of a sufficient length to reach an irradiation device 20 that is adjacent to but housed separately from the separation device.

With reference to FIG. 4, fluid circuit 200 may include inlet line 72, an anticoagulant (AC) line 74 for delivering AC from container 60, an RBC line 76 for conveying red blood cells from chamber 12 of container 14 to container 67, a platelet poor plasma (PPP) line 78 for conveying PPP to container 66 and line 80 for conveying mononuclear cells to and from blood processing container 14 and collection/illumination container 68. The blood processing set may include one or more venipuncture needle(s) for accessing the circulatory system of the patient. As shown in FIG. 4, fluid circuit 200 may include inlet needle 70 and return needle 82. In an alternative embodiment, a single needle may serve as both the inlet and outlet needle.

Fluid flow through fluid circuit 200 may be driven, controlled and adjusted by a microprocessor-based controller in cooperation with the valves, pumps, weight scales and sensors of device 10 and fluid circuit 200, the details of which are described in the aforementioned U.S. Pat. No. 6,027,657, although any suitable controller may be used.

In accordance with the present disclosure, the fluid circuit may be further adapted for association with the irradiation device 20. One example of a suitable irradiation device is described in U.S. Pat. No. 7,433,030, which is incorporated by reference herein in its entirety, although any irradiation device may be used. The irradiation device 20 may include a tray or other holder for receiving one or more containers during treatment.

Figure 5:
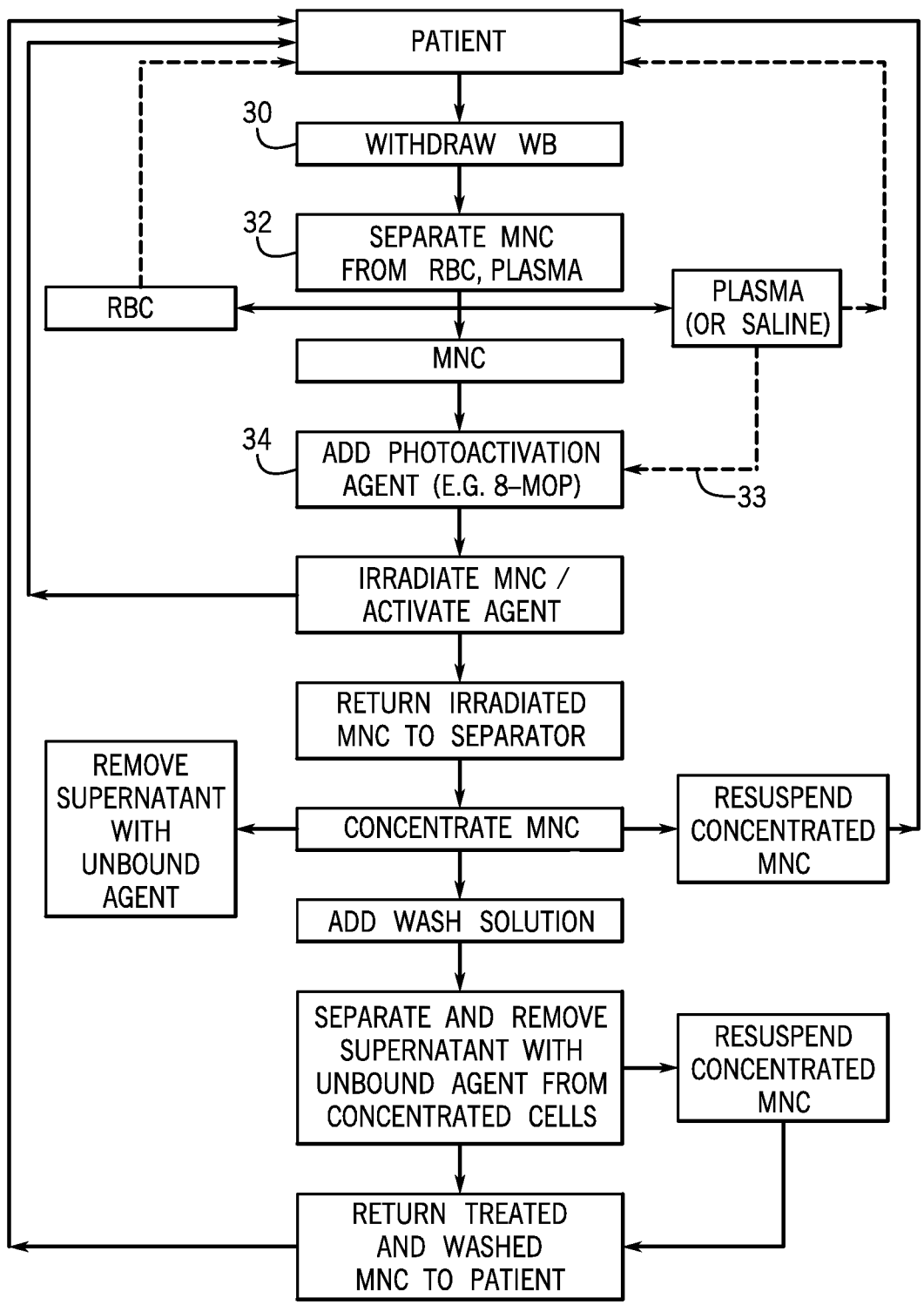
FIG. 5 is a flow chart setting forth a portion of the steps of the method of a photopheresis treatment, according to an exemplary embodiment.

FIG. 5 depicts one embodiment of an online method of treating mononuclear cells. An "online" photopheresis system includes both the blood separation device and the irradiation device in an integrated system. An online system provides for reinfusion of treated target cells back to the patient. Whole blood may first be withdrawn from a patient (step 30) through inlet needle 70 and introduced into the separation chamber 12 of container 14 of processing set 200, where the whole blood is subjected to, for example, a centrifugal field. The centrifugal field may separate the target cell population, i.e., mononuclear cells, from red blood cells, platelets and plasma (step 32). The components such as red blood cells and platelets may be returned to the patient or may be diverted to a container (e.g., container 67) for further processing. Collection of the mononuclear cells may proceed in one or more cycles, with the number of processing cycles conducted in a given therapeutic procedure depending upon the total volume of MNCs to be collected. Although FIG. 5 depicts an online method of treating MNCs, offline methods are available as well. In offline methods, an apheresis device may be used to collect target cells. The collected target cells, typically contained in one or more collection containers, are severed or otherwise separated from the tubing set used during collection, where they are later treated in a separate irradiation or UV light device followed by subsequent reinfusion of the treated cells to a patient. During such offline methods, when the cells are transferred from the apheresis device to the irradiation device (which device may be located in another room or laboratory), communication with the patient is severed and the cells detached from the patient.

Collected target cells may be concentrated, diluted, or otherwise processed in preparation for irradiation within collection/illumination container 68 (FIG. 4). For example, collected target cells may be diluted with plasma and/or saline, e.g., at step 33 of FIG. 5, to achieve a desired hematocrit. Collected target cells may also be combined with a suitable photoactivation agent, e.g., step 34 of FIG. 5, in preparation for irradiation.

Figure 6:
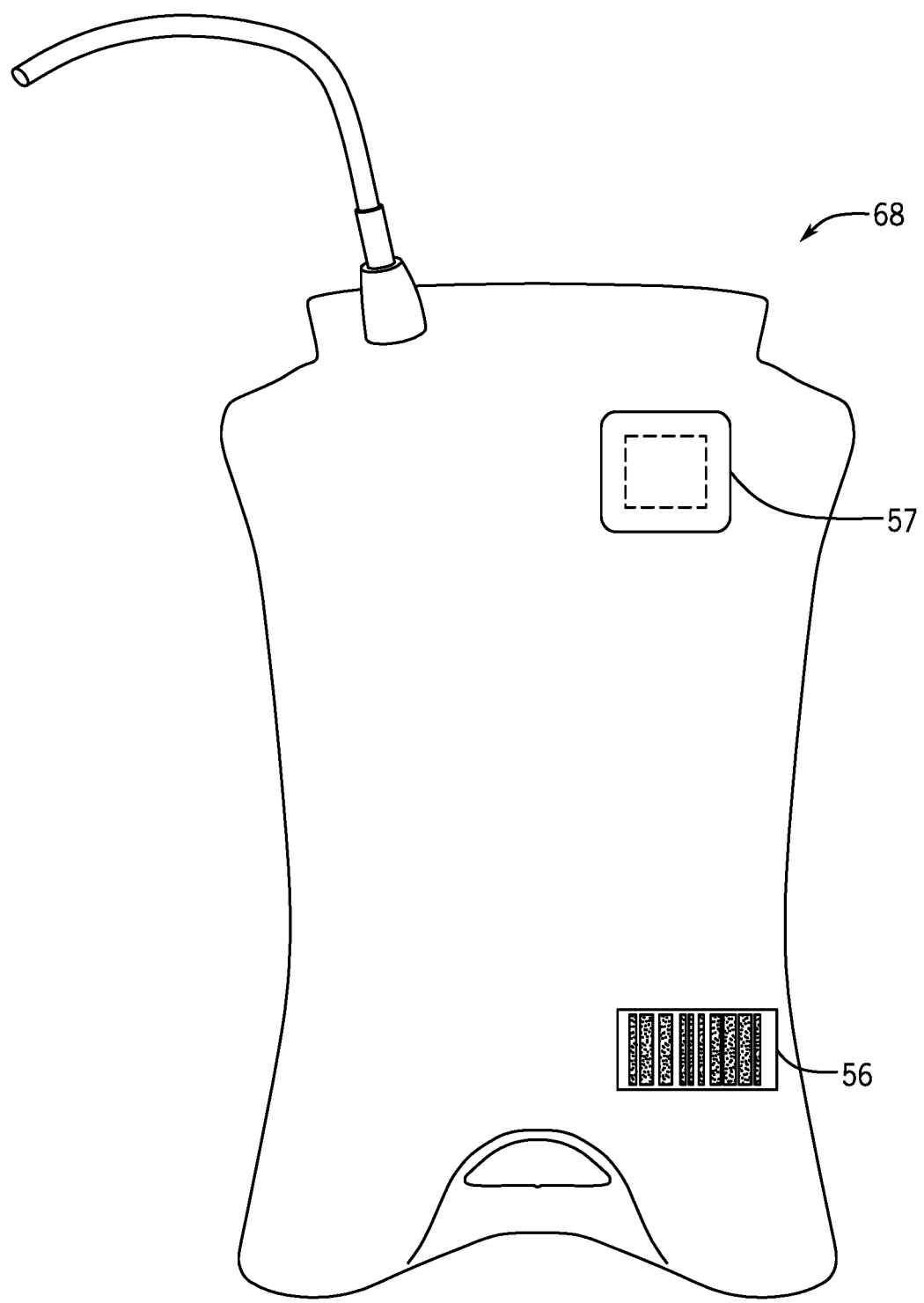
FIG. 6 shows an illumination container comprising features useful for labeling, tracking, and/or authenticating disposable components, according to an exemplary embodiment.

FIG. 6 shows an illumination container comprising features useful for labeling, tracking, and/or authenticating disposable components, according to an exemplary embodiment. In one embodiment, illumination container 68 that is part of disposable circuit 200 of FIG. 4 may comprise a tag 57 and/or a code 56 useful in preventing damage, alteration, falsification, and/or reuse of container 68 and/or any part of disposable circuit 200. Incorporating the tag 57 and/or code 56 onto container 68 may also prevent use of an otherwise legitimate disposable circuit intended for a different procedure performed by the system 5, separation component 10, and/or treatment component 20 (FIG. 1). For example, the system 5 may be programmed with a variety of other procedures, e.g., MNC collection (without photopheresis), platelet collection, offline photopheresis, etc., with each procedure having a corresponding and different disposable circuit. In an embodiment in which an authentication protocol is initiated for, e.g., an online photopheresis procedure, a user may be prevented from attempting to perform the online photopheresis procedure with a disposable circuit meant for, e.g., MNC collection, by scanning for the tag 57 and/or code 56 on container 68 to verify correctness of procedure and disposable circuit.

Tag 57 and/or code 56 may preferably maintain structural integrity during any storage period of container 68 and may preferably be covert as to attract minimal notice from users. The term "code" may be understood as an identification feature that provides relatively high labeling capacity or serialization. For example, a code may contain information decodable by a computer that may recognize a product and its details by cross-checking with established reference codes in a database. The term "tag" may be understood as an identification feature that provides limited labeling capacity and may be recognized by a computer but not decodable with information by the computer. For example, a tag may be used for simple authentication and/or tracking but may contain minimal information regarding the specific product.

In one embodiment, various molecules with characteristic optical emission may be used for the tag 57 and/or code 56 of container 68. A molecule with characteristic optical emission may be described as a molecule that is excited and isomerized by light close to certain wavelengths and will back-isomerize and generate emission at another wavelength when the excitation light is removed. For example, in an embodiment in which UV light is used to irradiate container 68 and its contents, a molecule that is isomerized by UV light and emits light at a non-UV wavelength when it is back-isomerized may be used. One example of UV-isomerized molecules with back-isomerization resulting in characteristic non-UV emission in the visible spectrum is photochromic ink. For example, various coumarin derivatives may isomerize in UV light and back-isomerize to emit green/yellow light having wavelengths in the range of 500-580 nm. Such coumarin derivatives include Coumarin 7 and Coumarin 30. In another example, colorless diarylethene derivatives incorporating trimethylsilyl (TMS) groups may isomerize in UV light, back-isomerize to emit blue light having wavelengths in the range of 455 to 492 nm, and in the presence of visible light, return to its colorless isomer.

Another embodiment may incorporate a molecule that is isomerized by UV light and emits light at near-infrared wavelengths when back-isomerized. Infrared emission may be desirable when it is intended for a tag/code to be invisible to the naked eye. Examples of molecules that are isomerized by UV light and emit light at infrared or near-infrared wavelengths of 700-850 nm when back-isomerized include various organic dyes, e.g., cyanine, oxazine, and rhodamine, and inorganic dyes, such as lanthanide-emitters. Another embodiment may incorporate different types of molecules with characteristic emission to create a unique fingerprint that is difficult to detect, ascertain, and/or replicate.

Figure 7:
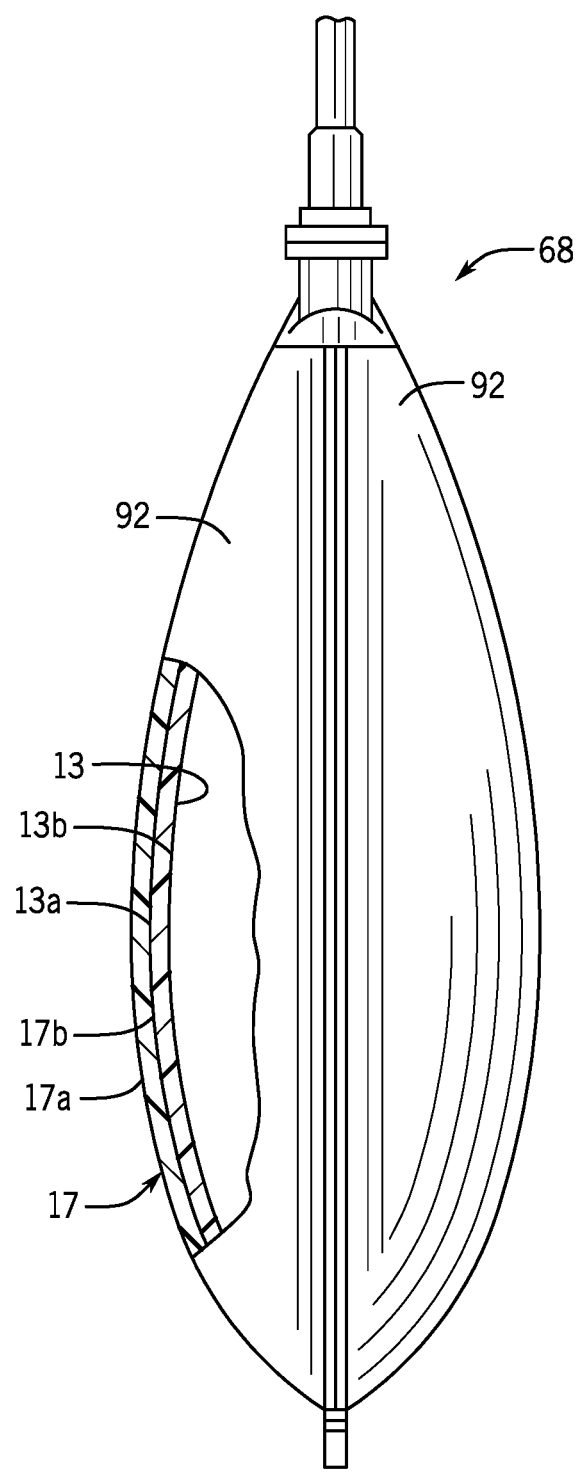
FIG. 7 shows a side view of the illumination container of FIG. 6, according to an exemplary embodiment.

A select molecule or combination of molecules with characteristic optical emission (hereinafter "photo-identifiable entity") may be dissolved in a solvent or ink suitable for printing on a medical device disposable component, such as container 68 (FIG. 4). An example of a printable ink is the photochromic textile screen ink available through QCR Solutions, Corp., although any suitable ink for medical devices may be used. A design, code, or pattern ("identifiable feature") formed by the photo-identifiable entity may be sensed, recognized, and/or decoded during irradiation or otherwise during a period in which the photo-identifiable entity is emitting photons. In an embodiment in which the disposable component to be tagged/coded is a fluid container such as the container 68 of FIG. 4, the substrate upon which the identifiable feature may be printed may be an inner or outer surface of the container 68. FIG. 7 shows a side view of container 68, according to an exemplary embodiment. In one embodiment, container 68 comprising container walls 92 may be made of a single layer of a polymer material, such as PVC or non-PVC polymer or polymer blend. In such a case, the identifiable feature may be printed or attached directly on the wall 92 of container 68. In another embodiment, container wall 92 may be made of a multiple sheet laminate wherein an inner layer 13 is made of one material and outer layer 17 is made of a different material. In such a case, the substrate upon which the identifiable feature may be printed may be separate from inner layer 13 and outer layer 17 and be placed between layers and form a part of the container wall 92. In another multi-layer embodiment, the identifiable feature may be printed on outer surface 17a of outer layer 17, inner surface 17b of outer layer 17, outer layer 13a of inner layer 13, and/or inner surface 13b of inner layer 13.

Figure 8A:
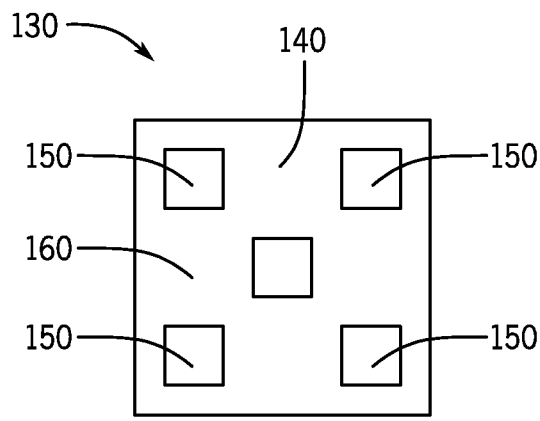
FIGS. 8A-8C show identifiable features detectable and recognizable by an authentication system, according to an exemplary embodiment.
Figure 8B:
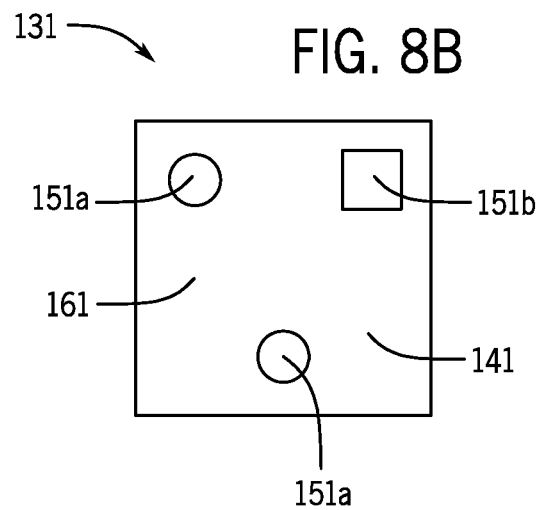
Figure 8C:
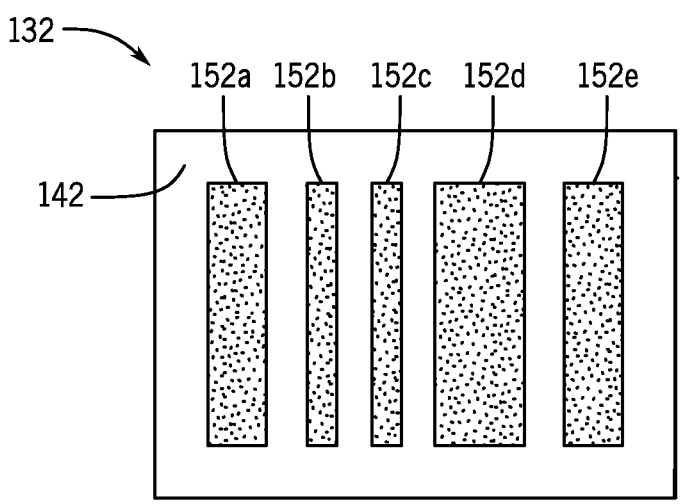

FIGS. 8A-8C show several examples of identifiable features. FIG. 8A shows an identifiable feature 130 comprising a substrate 140 upon which a photo-identifiable entity may be printed. Select areas 150 of the substrate 140 may comprise one photo-identifiable entity and the background 160 another photo-identifiable entity or no photo-identifiable entity. For example, areas 150 may be printed with a photo-identifiable entity comprising a compound that is isomerized by UV light and emits light at near-infrared wavelengths when back-isomerized, e.g., a lanthanide-emitter, while the background 160 comprises substrate 140 without any photo-identifiable entity. FIG. 8B shows an identifiable feature 131 comprising a substrate 141 upon which a plurality of photo-identifiable entities may be printed. Select areas 151a of the substrate 141 may comprise one photo-identifiable entity, select areas 151b a second photo-identifiable entity, and the background 161 a third photo-identifiable entity. For example, areas 151a may be printed with a photo-identifiable entity comprising a compound that is isomerized by UV light and emits yellow/green wavelength light when back-isomerized, e.g., a coumarin derivative, while areas 151b are printed with a photo-identifiable entity comprising a compound that is isomerized by UV light and emits blue wavelength light when back-isomerized, e.g., a TMS-incorporated diarylethene derivative, while the background 161 comprises substrate 141 without any photo-identifiable entity. FIG. 8C shows an identifiable feature 132 in the form of a barcode. Feature 132 may comprise bars 152a-152e that together contains coded information. Feature 132 may comprise a substrate 142 upon which bars 152a-152e having one or more photo-identifiable entities may be printed. In one embodiment, all bars 152a-152e may have the same photo-identifiable entity. In another embodiment, a specific combination and/or spatial arrangement of a plurality of photo-identifiable entities forming bars 152a-152e may form the barcode. Although FIG. 8C has been described as a barcode, it should be understood that the displayed code may be any suitable identifiable code, such as a QR code.

In another embodiment, an identification feature exhibiting expiration may be incorporated into an illumination container or any medical device disposable component to prevent reuse of the authentic component. The identification feature may comprise a curable resin/adhesive that is irreversibly cured by an excitation light source, e.g., UV light. A curable resin/adhesive prior to exposure to an excitation light source may be in an unlinked polymer state and emit/reflect/transmit one specific wavelength or set of wavelengths of light. In response to exposure to the excitation light source or shortly thereafter, the resin/adhesive may become cross-linked and emit/reflect/transmit a second specific wavelength or set of wavelengths of light. Examples of resin/adhesives that comprise one absorption spectra pattern prior to curing and another absorption spectra pattern during and/or after curing are various See-Cure products available from Dymax Corporation, To prevent accidental exposure to excitation light prior to use, the curable resin/adhesive may be covered until time of use of the disposable component. A disposable component incorporating curable resin/adhesive may be checked by a sensor or scanner to confirm that the resin/adhesive is in an uncured state prior to authorizing an irradiation procedure.

The curable resin/adhesive may be used in combination with various embodiments of the photo-identifiable entities described above to result in a disposable component that is simultaneously difficult to replicate and re-use. For example, a curable resin/adhesive may be incorporated into the barcode of FIG. 8C by overlaying the resin with one or more bars 152a-152e and/or adding bar(s) comprising curable resin. The barcode of FIG. 8C may emit/transmit a pattern of wavelengths of light differently when the resin is uncured versus when the resin is cured. For example, in an embodiment in which uncured resin is blue and cured resin is colorless, an irradiation device incorporating a sensor and a computer may first irradiate and scan prior to continuing the irradiation procedure to confirm that the received wavelengths of light and/or pattern of wavelengths of light initially includes blue light in addition to the pattern of photo-identifiable entities recognized by the device to approve and/or allow it to proceed with the procedure.

Figure 9:
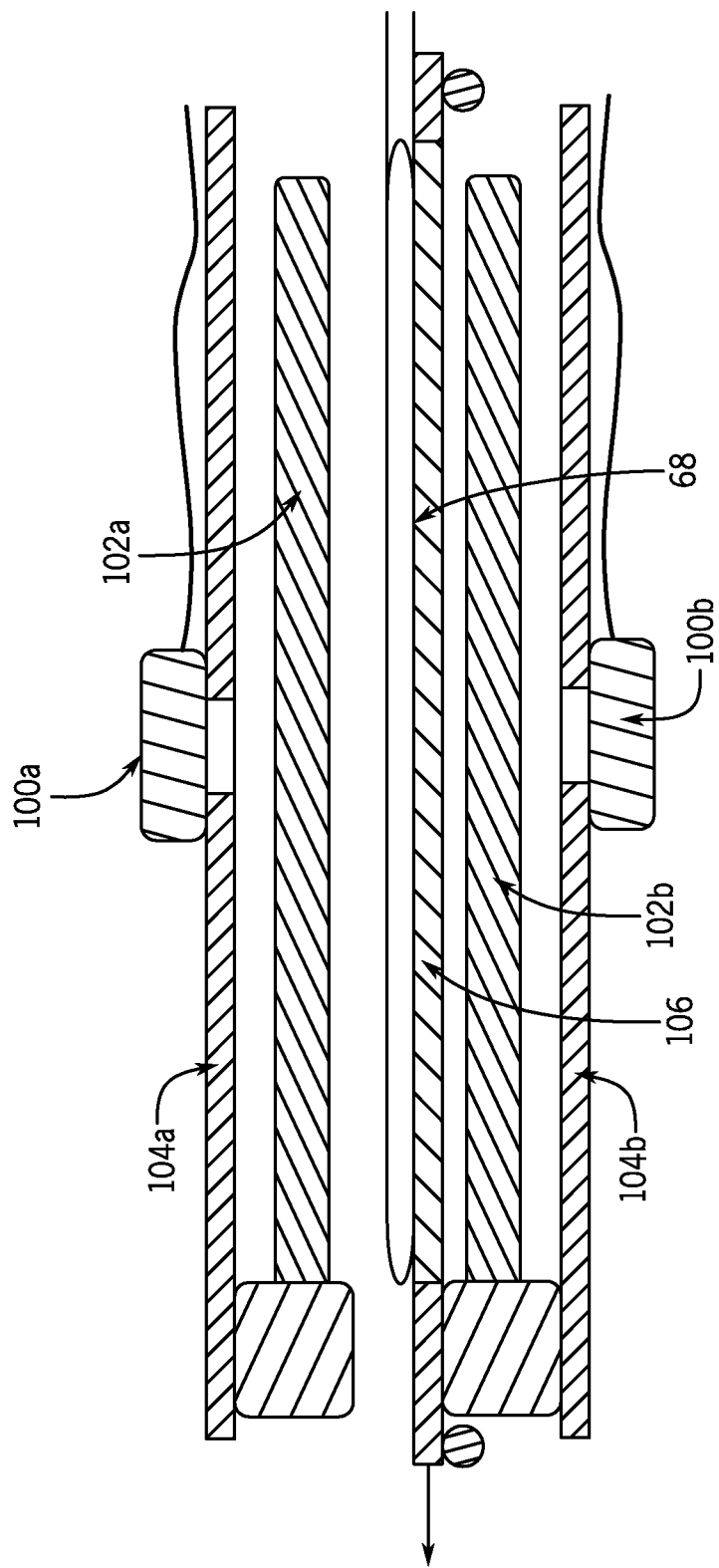
FIG. 9 is a cross-sectional view of the irradiation component of FIG. 1 holding an illumination container, according to an exemplary embodiment.

FIG. 9 shows a cross-sectional view of the irradiation component 20 of FIG. 1 holding container 68 having a tag 57 and/or code 56 (FIG. 6) and containing a target cell product. One or more irradiation receivers (e.g., sensors) 100a, sensitive to a specific set of wavelengths, may be mounted above an upper bank 102a of a plurality of irradiation transmitters (e.g., UV light bulbs). A reflector plate 104a may be disposed above the upper bank 102a of light bulbs to reflect light emitted by the bulbs. An exposure plane 106 comprised of material transparent to the specific range of wavelengths emitted by the upper bank 102a (e.g., UV-transparent material) may be disposed below the upper bank 102a of light bulbs to support illumination container 68. A lower bank 102b of a plurality of irradiation transmitters, e.g., UV light bulbs, may be disposed below the exposure plane 106. A second reflector plate 104b may be disposed below the lower bank 102b of irradiation transmitters to reflect light emitted by the light bulbs. One or more irradiation receivers (e.g., sensors) 100b, sensitive to the same or different range of wavelengths as receivers 100a, may be mounted below the lower bank 102b of the light bulbs. The irradiation device 20 may include any number of irradiation receivers 100a, 100b, depending on the number and sophistication of the tags 57 and/or codes 56, and the irradiation receivers 100a, 100b, may be tuned via filters to exclude frequencies of light other than the specific frequencies of light emitted/transmitted by the tags 57/codes 56, to minimize light interference.

In one embodiment, the one or more irradiation receivers 100a, 100b may comprise image sensors capable of mapping wavelength emissions/transmittance in 1D or 2D space.

CMOS and CCD sensors are examples of image sensors comprising a two-dimensional grid. Diodes sensitive to UV and/or infrared light outside the visible spectrum may be incorporated into the receivers 100a, 100b in an embodiment in which UV and IR wavelengths are to be recognized. The irradiation device may be configured to commence or proceed with irradiation when irradiation receivers 100a, 100b detect a recognized identifiable feature matching specific spatial, wavelength, intensity, and/or temporal characteristics.

Without limiting the foregoing description, in accordance with a first aspect of the subject matter herein, there is provided a computer-implemented method for approving a medical device disposable component used in a medical procedure. The method includes providing an identifiable feature on a medical device disposable component. The identifiable feature comprises one or more photo-identifiable entities having a first emission pattern when in an unexcited state and a second emission pattern when in an excited state. The identifiable feature is illuminated with an excitation light source to elicit the second emission pattern. The second emission pattern is detected and compared against a set of established reference emission patterns. Based on comparison of the second emission pattern to the set of established reference emission patterns, it is determined whether the medical device disposable component is approved.

In accordance with a second aspect which may be used or combined with the immediately preceding aspect, the medical procedure is continued if the second emission pattern is a match with the set of established reference emission patterns.

In accordance with a third aspect which may be used or combined with any of the preceding aspects, the first emission pattern is detected and it is determined whether the medical device disposable component is approved based on comparison of the first emission pattern to a second set of established reference emission patterns.

In accordance with a fourth aspect which may be used or combined with the immediately preceding aspect, a transformation from an unexcited state to an excited state for at least one photo-identifiable entity is irreversible.

In accordance with a fifth aspect which may be used or combined with any of the preceding aspects, detecting the second emission pattern comprises detecting at least one of wavelength range, two-dimensional location of wavelength emission, wavelength intensity, wavelength spatial sequence, and wavelength temporal sequence.

In accordance with a sixth aspect which may be used or combined with any of the preceding aspects, the one or more photo-identifiable entities comprises at least one of photochromic ink and curable adhesive.

In accordance with a seventh aspect which may be used or combined with any of the preceding aspects, the first and second emission patterns for at least one photo-identifiable entity do not comprise visible light.

In accordance with an eighth aspect which may be used or combined with any of the preceding aspects, a substrate is provided upon which one or more photo-identifiable entities are printed. The substrate is embedded within the medical device disposable component between a first layer and a second layer of a material of the disposable component.

In accordance with a ninth aspect which may be used or combined with any of the preceding aspects, the second emission pattern is detected by irradiation receivers comprising at least one of CMOS and CCD image sensors.

In accordance with a tenth aspect which may be used or combined with any of the preceding aspects, the excitation light source comprises UV light and the emission pattern comprises infrared light.

In accordance with an eleventh aspect, there is provided a medical device authentication and authorization system during a medical procedure. The system includes a durable medical device comprising an excitation light source and at least one irradiation receiver. A fluid circuit is configured to cooperatively associate with the durable medical device. The fluid circuit comprises a disposable component having an identifiable feature comprising one or more photo-identifiable entities having a first emission pattern when in an unexcited state and a second emission pattern when in an excited state. The system also includes a programmable controller. The programmable controller is configured to illuminate the identifiable feature with the excitation light source to elicit the second emission pattern, detect the second emission pattern with the at least one irradiation receiver, compare the second emission pattern against a set of established reference emission patterns, and determine whether the disposable component is approved based on comparison of the second emission pattern to the set of established reference emission patterns.

In accordance with a twelfth aspect which may be used or combined with the immediately preceding aspect, the programmable controller is further configured to proceed with the medical procedure if the second emission pattern is a match with the set of established reference emission patterns.

In accordance with a thirteenth aspect which may be used or combined with the eleventh or twelfth aspect, the programmable controller is further configured to detect the first emission pattern and determine whether the disposable component is approved based on comparison of the first emission pattern to a second set of established reference emission patterns.

In accordance with a fourteenth aspect which may be used or combined with the immediately preceding aspect, a transformation from an unexcited state to an excited state for at least one photo-identifiable entity is irreversible.

In accordance with a fifteenth aspect which may be used or combined with any of the eleventh through fourteenth aspects, the programmable controller comparing the second emission pattern against the set of established reference emission patterns comprises comparing at least one of wavelength range, two-dimensional location of wavelength emission, wavelength intensity, wavelength spatial sequence, and wavelength temporal sequence.

In accordance with a sixteenth aspect which may be used or combined with any of the eleventh through fifteenth aspects, the one or more photo-identifiable entities comprises at least one of photochromic ink and curable adhesive.

In accordance with a seventeenth aspect which may be used or combined with any of the eleventh through sixteenth aspects, the first and second emission patterns for at least one photo-identifiable entity do not comprise visible light.

In accordance with an eighteenth aspect which may be used or combined with any of the eleventh through seventeenth aspects, the disposable component comprises a first and second layer of one or more disposable component materials. A substrate upon which the one or more photo-identifiable entities are printed is disposed between the first and second layer.

In accordance with a nineteenth aspect which may be used or combined with any of the eleventh through eighteenth aspects, the irradiation receiver comprises at least one of CMOS and CCD image sensors.

In accordance with a twentieth aspect which may be used or combined with any of the eleventh through nineteenth aspects, the excitation light source comprises UV light and the second emission pattern comprises infrared light.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:

1. A computer-implemented method for approving a medical device disposable component used in a medical procedure and carrying out the medical procedure, the method comprising:
   providing an identifiable feature on a medical device disposable component, wherein the identifiable feature comprises one or more photo-identifiable entities having a first emission pattern when in an unexcited state and a second emission pattern when in an excited state;
   disposing the medical device disposable component and its contents within an irradiation device in which the medical procedure is carried out;
   enclosing the medical device disposable component and its contents within the irradiation device and illuminating the identifiable feature with an excitation light source configured to irradiate the medical device disposable component and its contents during the medical procedure to elicit the second emission pattern with the medical device disposable component and its contents disposed and enclosed within the irradiation device;
   detecting the second emission pattern via a sensor mounted on the irradiation device with the medical device disposable component and its contents disposed and enclosed within the irradiation device and comparing the second emission pattern against a set of established reference emission patterns;
   determining, using a computer, whether the medical device disposable component is approved based on comparison of the second emission pattern to the set of established reference emission patterns;
   proceeding to irradiate the medical device disposable component and its contents disposed and enclosed within the irradiation device with the excitation light source when the computer determines that the second emission pattern is a match with the set of established reference emission patterns; and
   not irradiating the medical device disposable component and its contents disposed and enclosed within the irradiation device with the excitation light source when the computer determines that the second emission pattern is not a match with the set of established reference emission patterns.

2. The computer-implemented method of claim 1, further comprising detecting the first emission pattern and determining whether the medical device disposable component is approved based on comparison of the first emission pattern to a second set of established reference emission patterns.

3. The computer-implemented method of claim 2, wherein a transformation from an unexcited state to an excited state for at least one photo-identifiable entity is irreversible.

4. The computer-implemented method of claim 1, wherein detecting the second emission pattern comprises detecting at least one of wavelength range, two-dimensional location of wavelength emission, wavelength intensity, wavelength spatial sequence, and wavelength temporal sequence.

5. The computer-implemented method of claim 1, wherein the one or more photo-identifiable entities comprises at least one of photochromic ink and curable adhesive.

6. The computer-implemented method of claim 1, wherein the first and second emission patterns for at least one photo-identifiable entity do not comprise visible light.

7. The computer-implemented method of claim 1, further comprising providing a substrate upon which one or more photo-identifiable entities are printed, wherein the substrate is embedded within the medical device disposable component between a first layer and a second layer of a material of the disposable component.

8. The computer-implemented method of claim 1, wherein the second emission pattern is detected by irradiation receivers comprising at least one of CMOS and CCD image sensors.

9. The computer-implemented method of claim 1, wherein the excitation light source comprises UV light and the second emission pattern comprises infrared light.

10. A medical device authentication and authorization system used with a medical device during a medical procedure, the system comprising:
   a medical device configured to receive and enclose a medical device disposable component and its contents within the medical device while the medical procedure is carried out, the medical device comprising an excitation light source configured to irradiate the medical device disposable component and its contents disposed and enclosed within the medical device during the medical procedure and at least one irradiation receiver mounted on the medical device;
   a fluid circuit configured to cooperatively associate with the medical device, the fluid circuit comprising the medical device disposable component having an identifiable feature comprising one or more photo-identifiable entities having a first emission pattern when in an unexcited state and a second emission pattern when in an excited state; and
   a programmable controller configured to:
      illuminate the identifiable feature with the excitation light source to elicit the second emission pattern with the medical device disposable component and its contents disposed and enclosed within the medical device;
      detect the second emission pattern with the at least one irradiation receiver with the medical device disposable component and its contents disposed and enclosed within the medical device;
      compare the second emission pattern against a set of established reference emission patterns;
      determine whether the disposable component is approved based on comparison of the second emission pattern to the set of established reference emission patterns;
      control the excitation light source to irradiate the medical device disposable component and its contents disposed and enclosed within the medical device when the second emission pattern is a match with the set of established reference emission patterns; and
      not control the excitation light source to irradiate the medical device disposable component and its contents disposed and enclosed within the medical device when the second emission pattern is not a match with the set of established reference emission patterns.

11. The medical device authentication and authorization system of claim 10, wherein the programmable controller is further configured to detect the first emission pattern and determine whether the disposable component is approved based on comparison of the first emission pattern to a second set of established reference emission patterns.

12. The medical device authentication and authorization system of claim 11, wherein a transformation from an unexcited state to an excited state for at least one photo-identifiable entity is irreversible.

13. The medical device authentication and authorization system of claim 10, wherein the programmable controller comparing the second emission pattern against the set of established reference emission patterns comprises comparing at least one of wavelength range, two-dimensional location of wavelength emission, wavelength intensity, wavelength spatial sequence, and wavelength temporal sequence.

14. The medical device authentication and authorization system of claim 10, wherein the one or more photo-identifiable entities comprises at least one of photochromic ink and curable adhesive.

15. The medical device authentication and authorization system of claim 10, wherein the first and second emission patterns for at least one photo-identifiable entity do not comprise visible light.

16. The medical device authentication and authorization system of claim 10, wherein the disposable component comprises a first and second layer of one or more disposable component materials, wherein a substrate upon which the one or more photo-identifiable entities are printed is disposed between the first and second layer.

17. The medical device authentication and authorization system of claim 10, wherein the irradiation receiver comprises at least one of CMOS and CCD image sensors.

18. The medical device authentication and authorization system of claim 10, wherein the excitation light source comprises UV light and the second emission pattern comprises infrared light.

19. The medical device authentication and authorization system of claim 10, wherein the second emission pattern comprises first and second lights emitted at different wavelengths.

20. The medical device authentication and authorization system of claim 10, wherein
the one or more photo-identifiable entities comprises a curable adhesive configured to be cured by the excitation light source, and
the second emission pattern is emitted after the curable adhesive has been cured by the excitation light source.

21. The medical device authentication and authorization system of claim 10, wherein
the excitation light source is configured to emit light having one or more wavelengths,
the at least one irradiation receiver is configured to receive light having at least one wavelength different from the one or more wavelengths of the light emitted by the excitation light source, and
the second emission pattern includes at least one wavelength different from the one or more wavelengths of the light emitted by the excitation light source.

* * * * *